(12) United States Patent
Gordley (10) Patent No.: US 9,952,146 B1
(45) Date of Patent: Apr. 24, 2018

(54) DETERMINING GAS CONCENTRATION NEAR PLANETARY SURFACES

(71) Applicant: G & A Technical Software, Inc., Newport News, VA (US)

(72) Inventor: Larry L. Gordley, Grafton, VA (US)

(73) Assignee: G & A TECHNICAL SOFTWARE, INC., Newport News, VA (US)

( * ) Notice: Subject to any disclaimer, the term of this patent is extended or adjusted under 35 U.S.C. 154(b) by 0 days.

(21) Appl. No.: 15/583,312

(22) Filed: May 1, 2017

(51) Int. Cl.
*G01N 21/3504* (2014.01)
*G01N 21/3518* (2014.01)

(52) U.S. Cl.
CPC ............... *G01N 21/3518* (2013.01)

(58) Field of Classification Search
CPC .......... G01N 21/3518; G01N 21/3504; G01N 2021/1793; G01N 2021/3531; G01N 2021/1795
See application file for complete search history.

(56) References Cited

U.S. PATENT DOCUMENTS 8,681,337 B2  5/2014  Gordley

OTHER PUBLICATIONS

Mercier ("Modeling, sensor design, and performance predictions for gas filter correlation radiometers", Sandia Report SAND2012-7985 Unlimited Release Sep. 2012, Prepared by Sandia National Laboratories Albuquerque, New Mexico 87185 and Livermore, California 94550).*

Tolton ("A Concept for a Gas-Filter Correlation Radiometer to Remotely Sense the Atmospheric Carbon Dioxide Column from Space", Boyd T. Tolton Synodon, Inc., Edmonton, Alberta, Canada May 9, 2003 and Nov. 27, 2003, http://journals.ametsoc.org/).*

* cited by examiner

*Primary Examiner* — Marcus Taningco
(74) *Attorney, Agent, or Firm* — Peter J. Van Bergen (57) ABSTRACT

A method and system are provided for determining gas concentration at a region of a planetary surface. A gas filter correlation radiometry (GFCR) system, provided at a location above a planetary surface, includes a processor and a GFCR sensor having a first gas cell containing a target gas and a second gas cell that does not contain the target gas. Using the GFCR sensor, first images of a region of the planetary surface are generated via capture through the first gas cell and second images of the region are generated via capture through the second gas cell. Using the processor, ratio images are generated using the first images and the second images. Concentration of the target gas over known altitude variations of the region is determined where the concentration of the target gas is a function of the ratio images and the altitude variations of the region.

20 Claims, 5 Drawing Sheets

DETERMINING GAS CONCENTRATION NEAR PLANETARY SURFACES

FIELD OF THE INVENTION

The invention relates generally to determining concentration of a gas in an atmosphere using optical remote sensors, and more particularly to a method and system for determining concentration of a gas near a planetary surface region using sensor signal changes induced by altitude variations of the planetary surface region.

BACKGROUND OF THE INVENTION

Sensing gas concentrations in Earth's lower atmosphere (e.g., the boundary layer) from an aircraft or an orbiting satellite/spacecraft equipped with passive sensors has been a formidable problem, especially for gases like carbon dioxide and methane whose detection is obscured by ambient amounts of gas in the upper atmosphere that mask the same gas in the boundary layer. The gas sensing task can be most difficult in the thermal infrared due to thermal contrast difficulties and water absorption. These difficulties are well-known in the art. Therefore, most passive sensor techniques rely on gas spectral features in the near infrared (i.e., wavelengths short of 3.5 microns) using scattered sunlight as the source. Attempts to make these measurements with various types of spectrometers have met with limited success since spectrally scanning spectrometer measurements of backscattered radiation from moving or spatially scanning instruments are difficult to interpret due to the highly variable nature of the scenes being imaged. The primary variability is the spectral and Bi-directional Reflectance Distribution Function (BRDF) character of the scattering surface. Static hyperspectral imaging instruments, such as Fabry-Perot spectrometers, overcome the spectral scanning problems, but face great difficulty in "stitching" together spectra from measurement samples as the scene locations pass through the spectrometer's field-of-view. Further, it is very difficult to calibrate and simulate the massive amounts of data in an analysis process. Still further, principal component analysis shows that sensitivity to the boundary layer is tenuous to begin with and is easily obscured by conditions of highly variable albedo and BRDF.

One method that addresses the complexity of spectra creation and calibration is a type of gas filtering commonly called Gas Filter Correlation Radiometry (GFCR). Briefly, in GFCR, a scene is viewed through gas cells having various amounts of a target gas (e.g., one cell filled with the target gas and one cell is empty). Spectral filtering is provided by the gas cell spectra and accurately-known cell gas content and conditions. The impact of albedo and BRDF variations will be the same for the multiple gas cell images regardless of gas cell condition, thereby nearly eliminating the error due to those effects. However, the only orbiting GFCR implementation to date with any success has been instrumentation that modulates the cell condition, which effectively modulates the sensitivity to only the target gas. Ideally, this is a major advantage. However, this implementation has two problems. First, the modulation induces a temporal change in filtering that can combine with the scene variability to create a temporal noise as the scene passes through the field-of-view. A second major problem is low sensitivity due to the inherently small modulation of the filtering function.

SUMMARY OF THE INVENTION

Accordingly, it is an object of the present invention to provide a method and system for determining gas concentrations near a planetary surface such as Earth's ground surface.

Another object of the present invention to provide a method and system for determining gas concentration at a planetary surface from a platform disposed in an atmosphere or space.

Still another object of the present invention is to provide a method and system for determining a target gas concentration over large regions of a planetary surface from an aircraft, satellite, or spacecraft.

Yet another object of the present invention is to provide a method and system for determining a target gas concentration near a planetary surface even when the target gas is present in atmospheric regions well above the planetary surface.

Other objects and advantages of the present invention will become more obvious hereinafter in the specification and drawings.

In accordance with an aspect of the present invention, a method and system are provided for determining gas concentration at a region of a planetary surface. A gas filter correlation radiometry (GFCR) system is provided at a location above a planetary surface. The GFCR system includes a processor and a GFCR sensor having a first gas cell containing a target gas and a second gas cell where the second gas cell does not contain the target gas. Using the GFCR sensor, first images of a region of the planetary surface are generated via capture through the first gas cell and second images of the region are generated via capture through the second gas cell. The method and system are provided with data on altitude variations of the region. Using the processor, ratio images are generated using the first images and the second images. Concentration of the target gas over the altitude variations of the region is determined using the processor where the concentration of the target gas is a function of the ratio images and the altitude variations of the region.

In accordance with another aspect of the present invention, column abundance of the target gas between the GFCR sensor and the planetary surface is determined. The column abundance of the target gas is a function of a first of the ratio images associated with a first zenith angle between the GFCR sensor and the planetary surface and a second of the ratio images associated with a second zenith angle between the GFCR sensor the planetary surface. The concentration of gas is a function of the ratio images, the altitude variations, and the column abundance

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
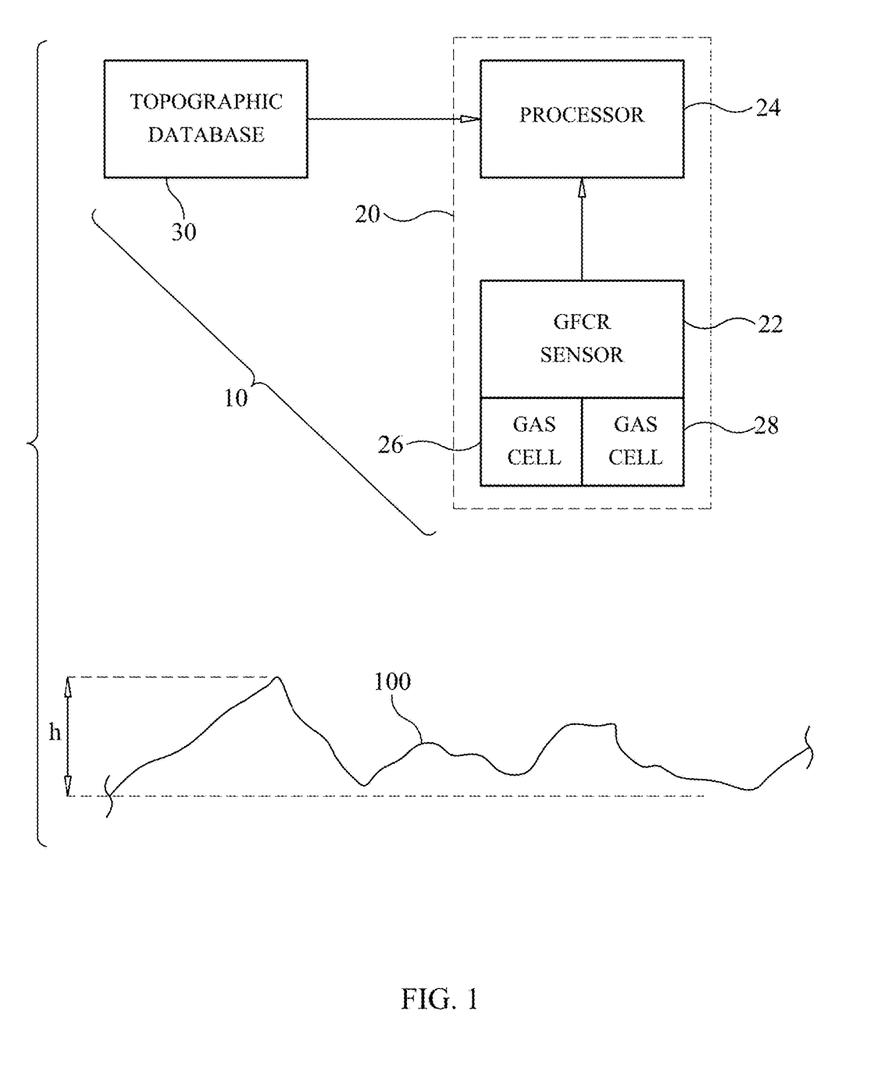
FIG. 1 is a top-level schematic view of a system for determining concentration of a target gas at a region of a planetary surface in accordance with an embodiment of the present invention.

Referring now to the drawings and more particularly to FIG. 1, a top-level schematic view of a system for determining concentration of a target gas near a planetary surface 100 in accordance with an embodiment of the present invention is shown and is referenced generally by numeral 10. In general, gas concentration system 10 can be used/operated above any planetary surface 100 where the planet has an atmosphere that is illuminated by at least one source of celestial light that passes through the atmosphere and reflects off the planetary surface. It is to be understood that the term "planetary surface" as used herein includes a variety of light-reflecting features found at the surface of a planet to include all of the following:

- reflecting surfaces of naturally-occurring features of a planet's surface (e.g., rocks, dirt, water, etc.),
- reflecting surfaces of naturally-occurring features that extend up from a planet's surface (e.g., vegetation such as trees), and
- reflecting surfaces of man-made features residing on a planet's surface (e.g., roads, buildings, pipelines, towers, etc.).

It is further assumed that the terrain presented by light-reflecting planetary surface 100 undulates or modulates such that reflecting points on surface 100 vary in altitude "h". By way of example, planetary surface 100 can be represented by the Earth's naturally-occurring and man-made surface features and the celestial source of light can be the Earth's sun.

System 10 includes a gas filter correlation radiometry (GFCR) system 20 and a database 30 of topographical data defining known altitude variations of planetary surface 100. GFCR sensor 22 can be any design of an imaging GFCR system that measures two identical images simultaneously. The system simply must create two identical independent beams. This can be done with independent telescopes or a single telescope in which the light is split to create two independent beams. The independent-beam type of GFCR sensor includes a first gas cell 26 containing a target gas and a second gas cell 28 that does not contain the target gas (e.g., gas cell 28 can contain a vacuum). As used herein, the phrase "target gas" refers to a gas of interest, the concentration of which system 10 is capable of determining near planetary surface 100. Such target gases of interest could include, but are not limited to, methane, ammonia, [13]carbon dioxide, nitrous oxide, carbonyl sulfide, hydrogen chloride, and hydrogen fluoride. An exemplary independent-beam GFCR sensor is described in U.S. Pat. No. 8,681,337, the contents of which are hereby incorporated by reference.

In terms of its general operation, system 10 is located above planetary surface 100 onboard a platform (not shown in FIG. 1) that can be an aircraft or orbiting vehicle. That is, system 10 can be located in an atmospheric region above planetary surface 100 or in space above the atmospheric region. GFCR sensor 22 captures images of the same region of planetary surface 100 where a first image is captured through gas cell 26 and a second image is captured through gas cell 28. In accordance with the teachings in the above-referenced U.S. Pat. No. 8,681,337, the captured first and second images for a region of planetary surface 100 are used to generate ratio images using processor 24. Then, in accordance with the present invention and as will be explained in greater detail below, processor 24 determines concentration of a target gas (i.e., the target gas in gas cell 26) near the region of planetary surface 100 using the ratio images and known altitude variations of the region. Since the GFCR-based ratio images are insensitive to variations in albedo and BRDF, so too are the determinations of target gas concentrations.

Figure 2:
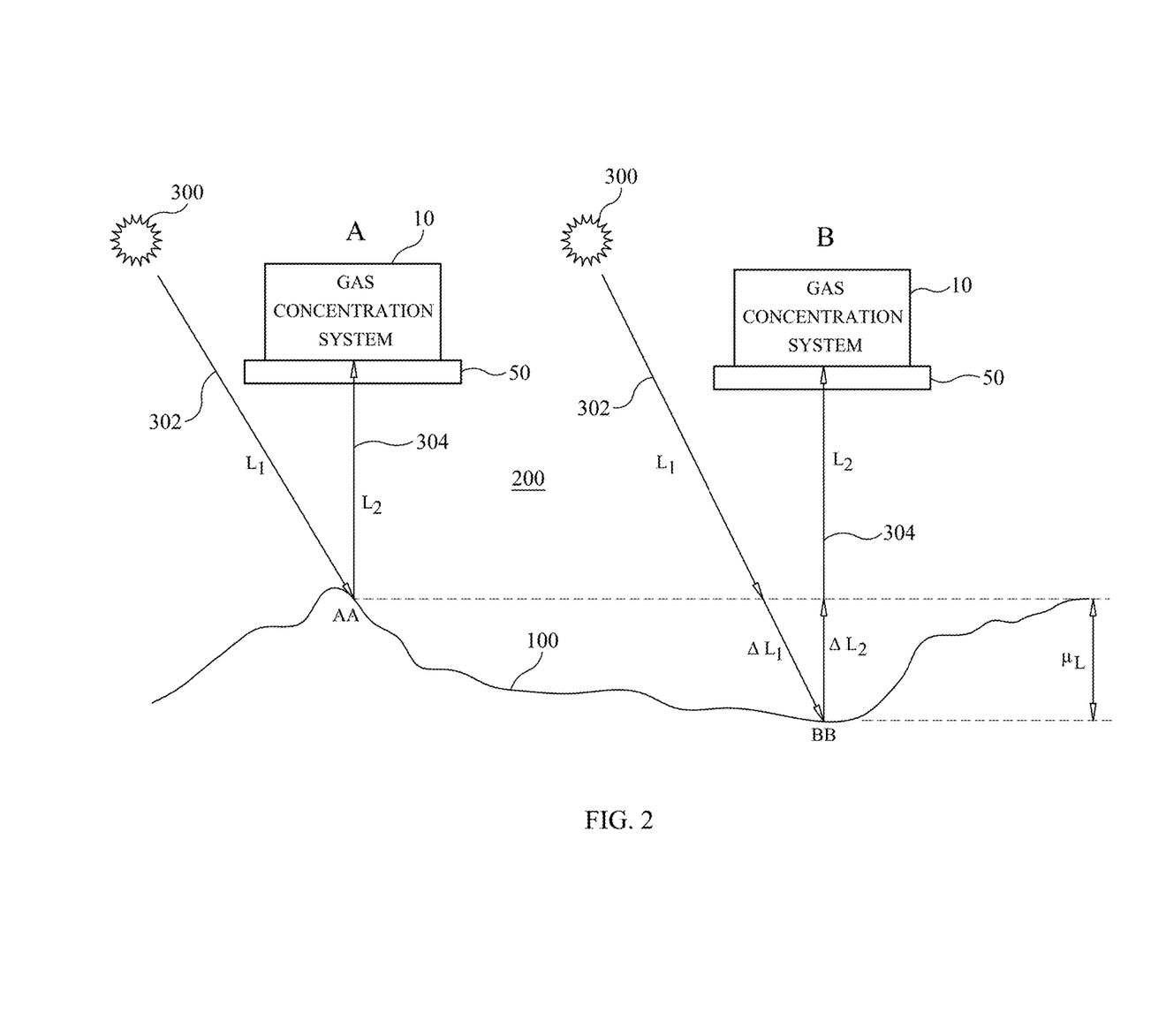
FIG. 2 is a diagrammatic view of an operational sequence of the present invention in which the system is operated above a planetary surface having a modulating-altitude terrain.

Referring now to FIG. 2, an operational sequence for determining gas concentration near planetary surface 100 using gas concentration system ("GCS") 10 will now be described. It will be assumed that an atmosphere 200 is above planetary surface 100 and that at least one celestial light source 300 (e.g., Earth's sun when planetary surface 100 is Earth's surface) produces light energy that illuminates and passes through atmosphere 200 and reflects off planetary surface 100. System 10 resides onboard a platform 50 that can be an aircraft, satellite, spacecraft, etc., above planetary surface 100. Platform 50 can be moving or stationary with respect to planetary surface 100. For purpose of the following operational description, it is assumed that platform 50 travels from location A to location B over planetary surface 100.

At location A, light 302 from source 300 travels a distance $L_1$ to a region "AA" on planetary surface 100 and reflects therefrom as reflected light 304. Using reflected light 304 that travels a distance $L_2$ to system 10, first and second gas cell images of planetary surface 100 at region AA are generated by system 10 along with corresponding ratio images as mentioned above. At location B, light 302 travels a distance $(L_1+\Delta L_1)$ to a region "BB" on planetary surface 100 that is at a different altitude than region AA (e.g., lower as shown or higher). Light 304 reflecting from planetary surface 100 to system 10 travels a distance $(L_2+\Delta L_2)$. System 10 generates first and second gas cell images of planetary surface 100 at region BB, and generates corresponding ratio images.

The following mathematical description is presented to provide an understanding of the implementation of the present invention. However, it is to be understood that while the method of the present invention is not mathematically rigorous, equations presented in the following description convey an empirical understanding of the present invention. For simplicity, the equations presented below apply to monochromatic wavelengths even though typical GFCR uses finite broadband spectra. However, the following description and accompanying illustrations provide a clear understanding of the inventive approach.

As described briefly above, the present invention includes the creation of two identical or nearly identical images within the limits of imaging hardware, calibration of the imaging hardware, and image analysis techniques. For one image, the sensitivity to a target gas is removed by passing light through a gas cell filled with a sample of the target gas thereby blocking light affected by the target gas in the imaged scene. The second image is generated by passing the same light through another gas cell that does not contain the target gas. Then, a ratio image ($R_I$) is created by dividing one image by the other. The ratio image $R_I$ has the unique property of being nearly insensitive to anything other than changes in the column abundance of the target gas. By observing and quantifying one or two known forms of column length modulation (i.e., terrain height by itself or terrain height and observation zenith angle), the resulting ratio image $R_I$ variations are used to infer near-surface target gas concentration ($q_L$) and total path column abundance (u) independently and simultaneously. For cases where a target gas will only be found near a planetary surface (e.g., ammonia, hydrogen fluoride, hydrogen chloride), or cases where the ambient total path column provides weak absorption (e.g., nitrous oxide, carbonyl sulfide), the present invention need only use altitude variations of a planetary surface region being imaged. However, in cases where a target gas has ambient concentrations in atmospheric regions well above a planetary surface (e.g., methane, $^{(13)}$carbon dioxide), the present invention will use altitude variations of the planetary surface region as well as the target gas's total column abundance determined using various zenith angle observations as will be explained further below. For most cases, the ambient total column abundance is known sufficiently well to accurately model or provide the required knowledge of sensitivity (i.e., the variable C in equation (1)) of $R_I$ to near-surface gas. Therefore, zenith angle observations for most applications will serve as redundant information to improve result confidence.

For the terrain modulation of planetary surface 100 as shown in FIG. 2, it can be shown that:

$$R_{IAA} - R_{IBB} = \Delta R_I = Cu_L \quad (1)$$

where $C = \delta R_I / \delta u_L$ and $u_L = q_L \Delta L_T$
and where $R_{IAA}$ & $R_{IBB}$ are ratio image values for points AA and BB, respectively, C is the change in $R_I$ per change in column abundance of the lower layer and is a function of the atmosphere column abundance u above the $\Delta L$ layer, $q_L$ is the mean mixing ratio or gas concentration of the target gas over the $\Delta L$ layer, $u_L$ is the ray path column abundance for the $\Delta L$ layer, and
$\Delta L_T = \Delta L_1 + \Delta L_2$, i.e., known from altitude variation data available from topological maps.

The ultimate objective is to determine $q_L$, which can be found by solving equation (1) as follows:

$$q_L = (R_{IAA} - R_{IBB})/(C\Delta L_T) \quad (2)$$

Figure 3:
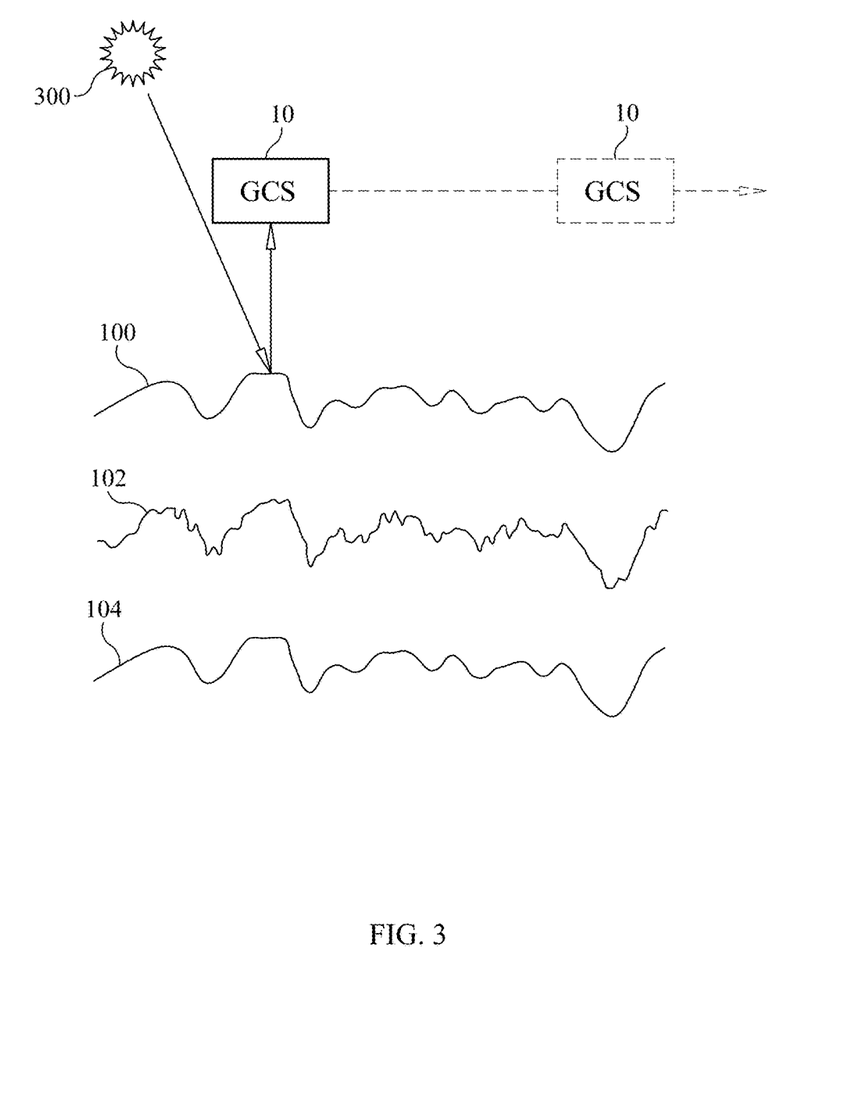
FIG. 3 is a two-dimensional diagrammatic view of a method for determining concentration of a target gas at a region of a planetary surface in accordance with an embodiment of the present invention.

Referring now to FIG. 3, the present invention can also be explained via a statistical inference of $q_L$ by using ($R_{IAA} - R_{IBB}$) measurements to calculate terrain $\Delta L_T$ values and comparing the calculated $\Delta L_T$ to the actual value thereof available using known topographical maps. More specifically, curve 102 represents the shape of planetary surface 100 that can be inferred from $R_I$ and a guessed value of gas concentration $q_L$ as system ("GCS") 10 operates above planetary surface 100. Curve 104 represents the shape of planetary surface 100 that can be generated from known topographical data. Accordingly, implementation of the present invention can be accomplished by iteration processing where multiple guessed values of $q_L$ are used in a curve fitting iteration process. That is, the value of $q_L$ yielding a match (or near match) between curves 102 and 104 yields the gas concentration $q_L$ over the near-surface L layer of the atmosphere. In practice, a large focal plane array detector observing a large area can supply on the order a million measurements within one ratio image with each ratio image providing a measure of $q_L$. Each of these single measurements will have substantial noise, but the statistical average will provide extremely accurate and precise results.

Figure 4A:
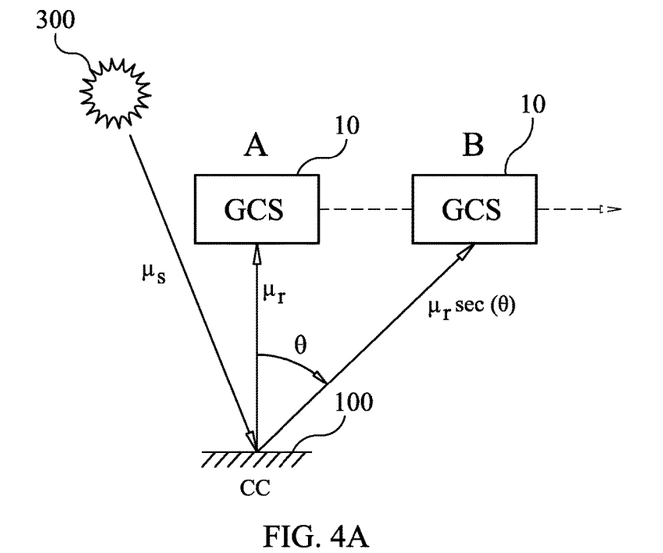
FIG. 4A is a diagrammatic view of a first approach used to obtain zenith angle measurements where such measurements are used to determine total column abundance of a target gas.
Figure 4B:
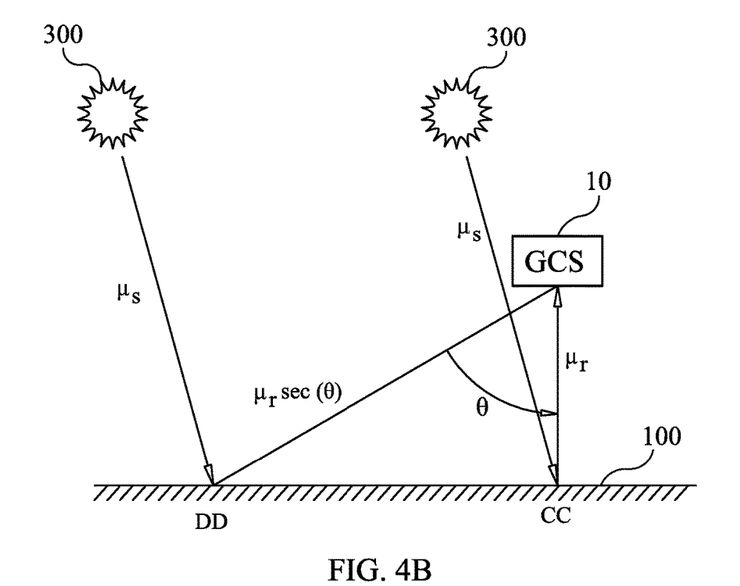
FIG. 4B is a diagrammatic view of a second approach used to obtain zenith angle measurements where such measurements are used to determine total column abundance of a target gas.

Note that the C function will vary with the temperature and pressure profile of the entire atmosphere, and the total column abundance along the path from source 300 to surface 100 or $u_s$, and reflected path from surface 100 to system 10 or $u_r \sec(\theta)$ as shown in FIG. 4. But tables of C values as a function of various atmospheric conditions can be pre-calculated and catalogued, reducing the processing to a table lookup.

As mentioned above, for gases with significant total column abundances, the target gas concentration in the upper atmosphere columns needs to be known. For most gases of interest, the upper atmosphere columns are either insignificant or adequately known from other sources, allowing accurate C values. However, the present invention can also determine the total column abundance ($u_r$) from the $R_I$ images using zenith modulation measurements. Referring to FIGS. 4A and 4B, two approaches are illustrated for making zenith angle observations/measurements that can be used to determine total column abundance of a target gas. FIG. 4A illustrates a first approach where zenith angle observations are made by GCS 10 of position CC on planetary surface 100 from two different zenith locations A and B. FIG. 4B illustrates a second approach where zenith angle observations are made by GCS 10 of positions CC and DD on planetary surface 100 from a single location A where positions CC and DD are assumed to have the same surface reflecting elevation. Since celestial light source 300 is located a great distance from planetary surface 100 as compared to GCS 10, the $u_s$ vectors are essentially parallel to one another. For purpose of illustration, celestial light source 300 is duplicated in FIG. 4B in order to illustrate the parallel nature of the $u_s$ vectors.

The observation of the same location from two different zenith angle positions (or the observation of two different but same reflecting-elevation locations from a single position) enables the inference of the vertical column abundance $u_r$ of the target gas for the atmosphere between the planetary surface and GCS 10. For example, using the approach illustrated in FIG. 4A, the observations of the surface position from satellite positions A and B are made through the same atmospheric layer to the same surface point. But, the path length of the upwelling light through all levels of the atmosphere is increased by a factor of sec(e) for the B position observation thereby providing the inference of $u_r$. A similar result occurs using the approach illustrated in FIG. 4B.

The ratio image or $R_I$ values can be shown to have a mathematical behavior similar to broadband transmission $\tau$ (or absorption 1−$\tau$). However, the concept is more easily illustrated (with reference to FIG. 4) with a monochromatic formulation of transmission where the following can be shown:

$$u_r = \ln(\tau_A/\tau_B)/[\sigma(\sec\theta - 1)] \quad (3)$$

where $u_r$ is the column abundance for path CC to A, $\tau_A$ is the transmission of the target gas along path CC to A, $\tau_B$ is the transmission of the target gas along path CC to B, and $\sigma$ is the target gas cross section.

The broadband transmission scenario presents similar physical relationships while being mathematically more complicated. Nevertheless, the result is that the ratio image $R_I$ measurements have the information content required to allow total atmosphere column abundance measurements sufficient for retrieving accurate surface level concentrations. As a result, the approach described herein can be used to infer surface elevation using data obtained from either moving (e.g., aircraft, satellites, spacecraft, etc.) or fixed platforms (e.g., balloons) by applying the principles described above.

Figure 5A:
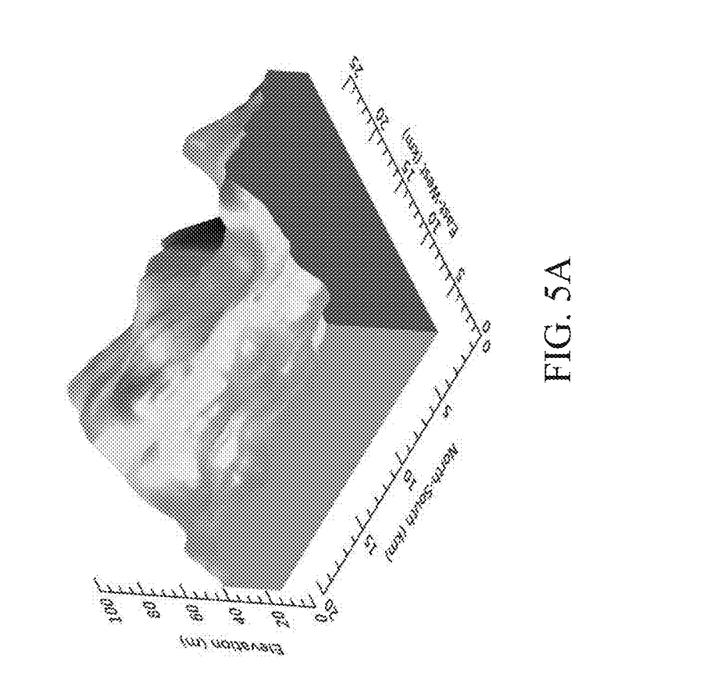
FIG. 5A is an exemplary three-dimensional elevation contour map of a planetary surface region developed from known topographical data.
Figure 5B:
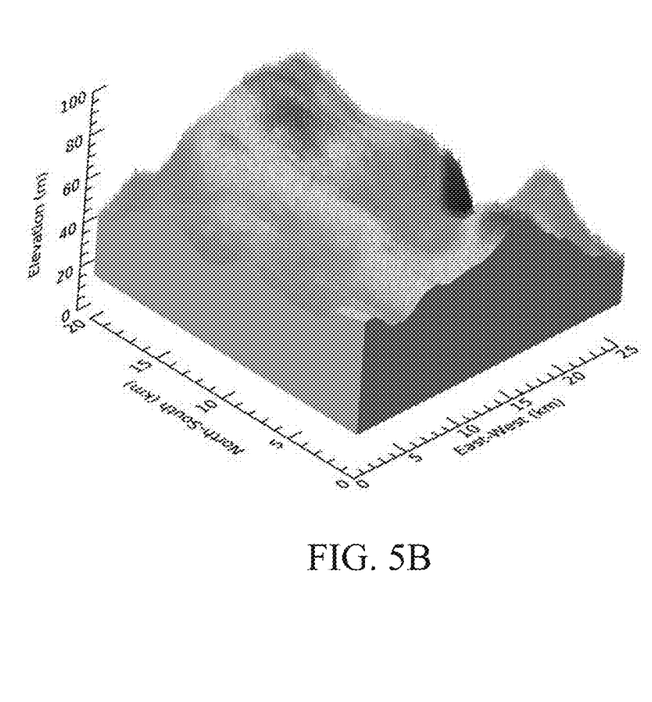
FIG. 5B is an inferred three-dimensional contour map generated using ratio images in accordance with the present invention.

The statistical power of the present invention can be seen with reference to FIGS. 5A and 5B. In FIG. 5A, topological data is used to create a terrain elevation map that coincides with an observation. Then, a modeled gas correlation ratio image is used to create a "derived" elevation map for a chosen region of the ratio image (e.g., the full image in the illustrated example). This is done by using the ratio image measurement plus the following two assumed values:

the total gas column abundance above the terrain (obtained from ancillary information and/or the zenith observations), which allows the calculation of the differential value C in equation (1) above, and the mean mixing ratio of the target gas near the surface. The assumed gas mixing ratio near the surface is iterated until a best fit of the known terrain height to the "derived" terrain height is achieved. Note that for most gases, the near-surface gas concentration will not significantly affect the value of C, thereby allowing a direct calculation of $q_L$ without iteration. FIG. 5B illustrates an example (for the terrain contour illustrated in FIG. 5A) that has been rigorously "derived" using realistic methane column abundances, assumed scattering albedo of 10%, and spectral a bandpass near 2.29 microns.

The advantages of the present invention are numerous. Gas concentrations near a planetary surface are readily determined from air or space observation locations. The process and system of the present invention can make such gas concentration determinations for target gases that are only present near a planetary surface as well as for target gases that are simultaneously present in upper atmospheric regions. The present invention will find great utility in detecting gas leaks and their severity as well as suspected areas of impact. The present invention could also be used to track/monitor movement of a target gas over a planetary surface. The present invention is robust even in the presence of strong variation of albedo and BRDF.

Although the invention has been described relative to specific embodiments thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A method of determining gas concentration at a region of a planetary surface, comprising the steps of:

providing a gas filter correlation radiometry (GFCR) system at a location above a planetary surface, said GFCR system including a processor and a GFCR sensor having a first gas cell containing a target gas and a second gas cell wherein said second gas cell does not contain said target gas;

generating, using said GFCR sensor, first images of a region of the planetary surface captured through said first gas cell and second images of the region captured through said second gas cell;

providing data on altitude variations of the region indicative of a terrain elevation map of the region;

generating, using said processor, ratio images for the region using said first images and said second images; and iteratively generating, using said processor, a derived terrain elevation map of the region using said ratio images and values for a mixing ratio of said target gas and a column abundance of said target gas wherein concentration of said target gas above the region is indicated when a best fit is achieved between said terrain elevation map and said derived terrain elevation map.

2. A method according to claim 1, wherein said location resides in one of an atmosphere above the planetary surface and space.

3. A method according to claim 1, wherein said location is onboard one of a moving platform and a stationary platform.

4. A method according to claim 1 further including the step of determining, using said processor, said column abundance of said target gas between said GFCR sensor and the planetary surface wherein said column abundance of said target gas is a function of a first of said ratio images associated with a first zenith angle between said GFCR sensor and the planetary surface and a second of said ratio images associated with a second zenith angle between said GFCR sensor and the planetary surface.

5. A method according to claim 1, wherein said first images and said second images are generated using light reflected from the planetary surface.

6. A method according to claim 1, wherein said first images and said second images are generated using light originating from at least one celestial source of light.

7. A method of determining gas concentration at a region of a planetary surface, comprising the steps of:

providing a gas filter correlation radiometry (GFCR) system at a location above a planetary surface having an atmosphere illuminated by celestial light wherein the celestial light passes through the atmosphere and reflects off the planetary surface as reflected light, wherein at least a portion of the atmosphere resides between the location and the planetary surface, said GFCR system including a processor and a GFCR sensor having a first gas cell containing a target gas and a second gas cell wherein said second gas cell does not contain said target gas;

detecting, using said GFCR sensor, the reflected light associated with a region of the planetary surface;

generating, using said GFCR sensor, first images of the region based on the reflected light passing through said first gas cell and second images of the region based on the reflected light passing through said second gas cell;

providing said processor with data on altitude variations of the region indicative of a terrain elevation map of the region;

generating, using said processor, ratio images for the region using said first images and said second images; and iteratively generating, using said processor, a derived terrain elevation map of the region using said ratio images and values for a mixing ratio of said target gas and a column abundance of said target gas wherein concentration of said target gas above the region is indicated when a best fit is achieved between said terrain elevation map and said derived terrain elevation map.

8. A method according to claim 7, wherein said location resides in one of an atmosphere above the planetary surface and space.

9. A method according to claim 7, wherein said location is onboard one of a moving platform and a stationary platform.

10. A method according to claim 7 further including the step of determining, using said processor, said column abundance of said target gas between said GFCR sensor and the planetary surface wherein said column abundance of said target gas is a function of a first of said ratio images associated with a first zenith angle between said GFCR sensor and the planetary surface and a second of said ratio images associated with a second zenith angle between said GFCR sensor and the planetary surface.

11. A system for determining gas concentration at a region of a planetary surface, comprising:
a platform disposed at a location above a planetary surface;
a gas filter correlation radiometry (GFCR) system disposed on said platform, said GFCR system including a processor and a GFCR sensor having a first gas cell containing a target gas and a second gas cell wherein said second gas cell does not contain said target gas, said GFCR sensor directed towards a region of the planetary surface, said GFCR sensor generating first images of the region captured through said first gas cell and second images of the region captured through said second gas cell;
a database of known altitude variations indicative of a terrain elevation map of the region, said database being coupled to said processor;
said processor generating ratio images of the region using said first images and said second images; and
said processor iteratively generating a derived terrain elevation map of the region using said ratio images and values for a mixing ratio of said target gas and a column abundance of said target gas wherein concentration of said target gas above the region is indicated when a best fit is achieved between said terrain elevation map and said derived terrain elevation map.

12. A system as in claim 11, wherein said platform resides in one of an atmosphere above the planetary surface and space.

13. A system as in claim 11, wherein said platform is selected from the group consisting of a moving platform and a stationary platform.

14. A system as in claim 11, wherein said processor determines said column abundance of said target gas between said GFCR sensor and the planetary surface wherein said column abundance of said target gas is a function of a first of said ratio images associated with a first zenith angle between said GFCR sensor and the planetary surface and a second of said ratio images associated with a second zenith angle between said GFCR sensor and the planetary surface.

15. A system as in claim 11, wherein said first images and said second images are generated using light reflected from the planetary surface.

16. A system as in claim 11, wherein said first images and said second images are generated using light originating from at least one celestial source of light.

17. A system for determining gas concentration at a region of a planetary surface, comprising:
a gas filter correlation radiometry (GFCR) system adapted to be disposed on a platform at a location above a planetary surface, said GFCR system including a processor and a GFCR sensor having a first gas cell containing a target gas and a second gas cell wherein said second gas cell does not contain said target gas, said GFCR sensor directed towards a region of the planetary surface, said GFCR sensor generating first images of the region captured through said first gas cell and second images of the region captured through said second gas cell;
a database of known altitude variations indicative of a terrain elevation map of the region, said database being coupled to said processor;
said processor generating ratio images of the region using said first images and said second images; and
said processor iteratively generating a derived terrain elevation map of the region using said ratio images and values for a mixing ratio of said target gas and a column abundance of said target gas wherein concentration of said target gas above the region is indicated when a best fit is achieved between said terrain elevation map and said derived terrain elevation map.

18. A system as in claim 17, wherein said processor determines said column abundance of said target gas between said GFCR sensor and the planetary surface wherein said column abundance of said target gas is a function of a first of said ratio images associated with a first zenith angle between said GFCR sensor and the planetary surface and a second of said ratio images associated with a second zenith angle between said GFCR sensor and the planetary surface.

19. A system as in claim 17, wherein said first images and said second images are generated using light reflected from the planetary surface.

20. A system as in claim 17, wherein said first images and said second images are generated using light originating from at least one celestial source of light.

* * * * *